United States Patent [19]

Kimura et al.

[11] Patent Number: 4,598,046
[45] Date of Patent: Jul. 1, 1986

[54] MUTANT STRAIN OF *ESCHERICHIA COLI* AND ITS USE FOR THE PREPARATION OF GLUTATHIONE

[76] Inventors: Akira Kimura, 80-2, Wakamiya-dori 6-jo-agaru, Kami-wakamiya-cho, Shimogyo-ku, Kyoto-shi, Kyoto-fu; Kousaku Murata, 3-35, Nishino Hitsugawa-cho, Yamashina-ku, Kyoto-shi, Kyoto-fu, both of Japan

[21] Appl. No.: 690,385

[22] Filed: Jan. 10, 1985

Related U.S. Application Data

[63] Continuation of Ser. No. 402,697, Jul. 28, 1982, abandoned.

[30] Foreign Application Priority Data

Jul. 30, 1981 [JP] Japan .................. 56-120546

[51] Int. Cl.⁴ .................. C12P 21/02; C12N 15/00; C12N 11/18; C12N 1/20
[52] U.S. Cl. .................. 435/70; 435/172.3; 435/175; 435/253; 435/849; 935/14; 935/73
[58] Field of Search .................. 435/70, 128, 106, 175, 435/848, 849, 253, 172.3, 172.1; 935/27, 31, 56, 58, 73, 14

[56] References Cited

U.S. PATENT DOCUMENTS 4,237,224 12/1980 Cohen et al. .................. 435/172

FOREIGN PATENT DOCUMENTS 82099 7/1981 Japan .................. 435/70

*Primary Examiner*—Esther M. Kepplinger
*Attorney, Agent, or Firm*—Wolder, Gross & Yavner

[57] ABSTRACT

The present invention relates to a new mutant strain of *Escherichia coli* and its use for the preparation of glutathione.

The present invention is based upon the discovery that a certain mutant strain which we have induced from a wild strain of *Escherichia coli* is capable of accumulating large amounts of glutathione and an enzyme system for the synthesis of glutathione in the cultured broth.

The new mutant strain is preferably *Escherichia coli* designated *Escherichia coli* RC 912 p (FERM-BP No. 48).

8 Claims, No Drawings

MUTANT STRAIN OF ESCHERICHIA COLI AND ITS USE FOR THE PREPARATION OF GLUTATHIONE

This application is a continuation of application Ser. No. 402,697 filed on July 28, 1982, now abandoned.

The present invention relates to a new mutant strain of *Escherichia coli* and its use for the preparation of glutathione.

Glutathione is a kind of peptides, composed of L-glutamic acid, L-cysteine and glycine and is useful, for example, as a medicament for treating the liver disease, antidote and biochemical reagent. Conventionally, glutathione is prepared, for example, by extracting glutathione from the microbial cells of yeast; by placing a dried yeast having high permeability to membrane into contact with a substrate solution containing L-glutamic acid, L-cysteine and glycine; or by placing the microbial cells of yeast or coliform bacilli into contact with the substrate solution. With respect to the preparation of glutathione on an industrial scale, such known processes have however been characterized by poor yields.

The present invention is based upon the discovery that a certain mutant strain which we have induced from a wild strain of *Escherichia coli* is capable of accumulating large amounts of glutathione and an enzyme system for the synthesis of glutathione in the cultured broth.

Thus, an object of the present invention is to provide a new mutant strain of *Escherichia coli* and its use for the preparation of glutathione by fermentation. It has been found that by the use of the mutant strain of the present invention, it is possible to accumulate abundant quantities of glutathione as well as an enzyme system for the synthesis of glutathione from a substrate comprising L-glutamic acid, L-cysteine and glycine.

According to the present invention, there is provided a new mutant strain of *Escherichia coli* designated by us as *E. coli* RC912p (FERM-BP No. 48).

The mutant strain *E. coli* RC912p (FERM-BP No. 48) may be obtained by a process comprising the following steps:

(1) Preparation of a revertant strain of *E. coli*

A wild strain of *E. coli* such as *E. coli* B 355 (ATCC 23226, J. Appl. Biochem, 1, 283 (1979)), which is active upon γ-glutamyl-L-cysteine synthetase (E.C. 6.3.2.2, hereinafter referred to as GSH-I) and glutathione synthetase (E.C. 6.3.2.3, hereinafter referred to as GSH-II), is treated to induce a cysteine-requiring strain and a methylglyoxal-resistant strain. The induction of mutant strains may be effected in conventional manner, for example, by using N-methyl-N'-nitro-N-nitrosoguanidine (NTG), although it is also possible to use other mutagens such as the irradiation of ultraviolet ray if desired. After this, the treated strain is cultured by using a minimum medium containing L-cysteine ($2 \times 10^{-5}$M) and having a composition of $K_2HPO_4$ (0.7%), $KH_2PO_4$ (0.3%), $(NH_4)_2SO_4$ (0.1%), $MgSO_4.7H_2O$ (0.01%) and glucose (0.5%) [pH about 7.0; hereinafter referred to as DM medium] at a temperature of 30°–37° C. for 16–40 hours with shaking to obtain smaller colonies, from which a cysteine-requiring strain may be obtained and purely cultured under the same conditions. Separately, the strain after induction treatment is cultured under similar conditions by using a DM medium containing methylglyoxal ($2 \times 10^{-3}$M) to obtain larger colonies from which a methylglyoxal-resistant strain may be obtained. Then, the thus-obtained methylglyoxal-resistant strain is transferred to the above-mentioned DM medium containing the cysteine-requiring strain for culturing under the same conditions to obtain colonies having no halo around them, from which a mutant strain such as *E. coli* C 912 may be obtained. This strain which is deficient in the productivity of GSH-I is then treated with NTG in a similar manner to that described above to induce mutation, followed by culturing under the same conditions as described above by using a DM medium containing 8-hydroxyquinoline ($2 \times 10^{-4}$M) to obtain colonies, from which a mutant strain having an activity upon GSH-I and GSH-II and being released from the inhibition of GSH-I by glutathione is obtained.

The mutant strain thus-obtained is hereinafter referred to as revertant. A preferred strain of this type is exemplified by *E. coli* RC912 (FERM-BP No. 47).

(2) Isolation of chromosome DNA from the revertant

Isolation of chromosome DNA which involves the genetic information of GSH-I from the revertant and its purification may be effected in conventional manner, for example, by the phenol method [Biochim. Biophys. Acta. Vol. 72, pages 619–629 (1963)].

(3) Integration of the chromosome DNA into vector DNA

The thus-obtained chromosome DNA is integrated into a vector DNA to obtain a recombinant DNA. The integration may be effected in conventional manner. Thus, for example, the chromosome DNA and vector DNA are cut into pieces by using a suitable restriction endonuclease to obtain their fragments which are then mixed together and treated with a DNA ligase. The vector DNA which may be used for the purpose of the present invention includes, for example, pBR 322 plasmid, colicin (Col) El plasmid and lambda phage, having *Escherichia coli* as the host, and a particularly good result may be obtained by using pBR 322 plasmid. Preferred restriction enzymes which may be used are exemplified by Hin dIII, Eco RI, Pst I, Bam HI and the like and a better result may be obtained by using Hin dIII. With regard to DNA ligases which may be used for the purpose of the present invention, a DNA ligase originating from T4 phage is preferred.

(4) Introduction of the recombinant DNA into GSH-I deficient strain

Introduction of the recombinant DNA thus-obtained into a GSH-I deficient strain may be effected in conventional manner to obtain a GSH-I deficient strain involving the integrated recombinant DNA, for example, by treatment with calcium ion [Molec. gen. Genet., Vol. 124, pages 1–10 (1973)]. The method of selection of suitable strain involving the recombinant DNA, that is, the vector DNA, into which a foreign DNA involving the genetic information of GSH-I is integrated, may vary, with differring conditions, for example, the types of the restriction enzyme used for the preparation of the recombinant DNA of interest and the types of the vector DNA used. Thus, for example, when Hin dIII as a restriction enzyme and pBR 322 plasmid as a vector DNA are used, the selection may be effected in the following manner.

The used strain is cultured by using a DM medium as hereinbefore defined (pH about 7.0; 25°–37° C.; 16–40 hours) containing tetramethylthiuramdisulfide (40–90

μg/ml) and the resultant colonies are separated, followed by subsequent selection, effected with respect to the resistance to ampicillin, sensitivity to tetracycline and red colour appearing by applying nitroprusside-ammonia. The final selection is effected with respect to the presence or absence of glutathione in the microbial cells and of the activity upon GSH-I.

(5) Isolation of recombinant DNA from the strain

From the strain involving the recombinant DNA, obtained by the above-mentioned step, the recombinant DNA may be isolated in conventional manner, for example, by the alkali extraction method [Nucleic Acids Res., Vol. 7, pages 1513–1523 (1979)].

(6) Introduction of the recombinant DNA into the revertant

Introduction of the recombinant DNA into the revertant as hereinbefore defined i.e. the mutant strain which is active upon GSH-I and GSH-II and which is released from the inhibition of GSH-I activity by glutathione, may be effected in conventional manner, for example, by treatment with calcium ion [Molec. gen. Genet., Vol. 124, pages 1–10 (1973)] to obtain a revertant integrated with the recombinant DNA. The revertant integrated with the recombinant DNA (vector DNA integrated with foreign DNA involving the genetic information of GSH-I) may be obtained with reference to the colonies appearing on a DM medium containing ampicillin. A preferred example of the revertant obtained in this manner is $E.$ $coli$ RC912P (FERM-BP No. 48).

Preparation of glutathione (Process I)

By culturing the microorganism of the present invention, a large amount of glutathione is accumulated in the microbial cells. Both synthetic and organic media containing suitable carbon sources, nitrogen sources and inorganic substances may be used for this purpose. Examples of the carbon sources which may be used for culturing include glucose, sucrose, fructose, starch, starch hydrolyzate and various other hydrocarbons which may be used in an amount of 0.5–5.0%. Examples of the nitrogen sources which may be used include ammonium sulfate, ammonium phosphate, ammonium carbonate, ammonium acetate and various other inorganic and organic compounds containing ammonium; peptone, yeast extract, corn steep liquor, casein hydrolyzate and other inorganic substances containing nitrogen which may be used in an amount of 0.5–2.0%. Various inorganic substances such as potassium dihydrogen phosphate, dipotassium hydrogen phosphate, magnesium sulfate, manganese sulfate and the like may be used as inorganic substances in an amount of 0.005 to 0.5%. The culturing may be effected at a pH of 6–9, preferably 7–8.5 under aerobic conditions with shaking or with shaking and aeration. The culturing temperature may preferably be 25°–37° C. and the culturing time may preferably be 16–40 hours to accumulate a large amount of glutathione in the microbial cells.

After completion of the culturing, the glutathione accumulated in the microbial cells may be extracted, for example, with water by heating to 100° C. The isolation of glutathione from the extracted solution may be effected by suitable methods, for example, by treating the extracted solution with suitable ion exchange resin which is known per se.

Preparation of glutathione (Process II)

It is also possible to prepare glutathione by using the microbial cells and/or a material obtained by treating the microbial cells as an enzyme source which is placed into contact with a substrate solution comprising L-glutamic acid, L-cysteine and glycine to carry out an enzymatic reaction.

In this case, the expression "a material obtained by treating the microbial cells" denotes, for example, dried microbial cells, cell-free extract obtained by ultrasonic treatment of the microbial cells, enzyme obtained by purifying such a cell-free extracted solution, as well as immobilized microbial cells or immobilized purified enzyme obtained by immobilizing the microbial cells or purified enzyme in conventional manner (e.g. by entrapping with polyacrylamide gel or carrageenan gel).

The concentrations of L-glutamic acid, L-cysteine and glycine in the substrate solution are preferably and respectively 5–50 mM, 5–50 mM and 50–100 mM. The reaction may be effected at a pH of 6–9, preferably 7–8.5 and a temperature of 20°–50° C., preferably 30°–37° C.

In order to promote the enzymatic reaction, it is preferred to carry out the reaction in the presence of an adenosine-5'-triphosphate (ATP) regeneration system. In this case, it is possible to use as the ATP regeneration system, the reactions caused by various enzymes present in the microorganism used for the process of the present invention such as acetate kinase, enzymes for glycolysis, carbamylphosphate kinase, pyruvate kinase and the like. For example, the reaction may preferably be effected by using acetate kinase when 5–20 mM of magnesium ion as magnesium salt (for example, magnesium sulfate, magnesium chloride and the like), 2–5 mM of ATP and 5–10 mM of acetylphosphate are present in the substrate solution.

After completion of the reaction, glutathione accumulated in the reaction mixture may be isolated and purified in conventional manner, for example, by using suitable ion exchange resin. For example, the pH of the reaction solution is adjusted to about 3 with sulfuric acid and the solution is passed through a cation exchange resin such as Diaion PK-228 H+ (commercially available from Mitsubishi Kasei Kogyo K.K., Tokyo) to adsorb glutathione onto the resin, from which glutathione is eluted with about 0.5M ammonium hydroxide. The eluate is adjusted to a pH of about 4.5 with sulfuric acid and passed through an anion exchange resin such as Duolite A2 CH$_3$COO$^-$ form, (commercially available from Diamond Alkali Co., U.S.A.) to adsorb glutathione onto the resin. The adsorbed glutathione is eluted with 0.5M sulfuric acid. 50% ethanol is added to the eluate to give crystals of glutathione, followed by isolating the same.

The following non-limiting examples illustrate the present invention.

EXAMPLE 1

(1) Preparation of a revertant strain of $E.$ $coli$ RC912

$E.$ $coli$ B 355 (ATCC 23226), which is active upon γ-glutamyl-L-cysteine synthetase (E.C. 6.3.2.2, hereinafter referred to as GSH-I) and glutathione synthetase (E.C. 6.3.2.3, hereinafter referred to as GSH-II), is treated to induce a cysteine-requiring strain and a methylglyoxal-resistant strain. The induction of mutant strains was effected in conventional manner by using N-methyl-N'-nitro-N-nitrosoguanidine (NTG). After this, the treated strain was cultured by using a minimum medium containing L-cysteine ($2\times10^{-5}$M) and having a composition of $K_2HPO_4$ (0.7%), $KH_2PO_4$ (0.3%), $(NH_4)_2SO_4$ (0.1%), $MgSO_4.7H_2O$ (0.01%) and glucose (0.5%) [pH about 7.0; hereinafter referred to as DM medium] at a temperature of 37° C. for 24 hours with shaking to obtain smaller colonies, from which a cysteine-requiring strain was obtained and purely cultured under the same conditions. Separately, the strain after induction treatment was cultured under similar conditions by using a DM medium containing methylglyoxal ($2\times10^{-3}$M) to obtain larger colonies, from which a methylglyoxal-resistant strain was obtained. Then, the thus-obtained methylglyoxal-resistant strain was transferred to the above-mentioned DM medium containing the cysteine-requiring strain ($10^{-7}$ cells/ml) for culturing under the same conditions to obtain colonies having no halo around them, from which a mutant strain *E. coli* C 912 was obtained. This strain which is deficient in the productivity of GSH-I was then treated with NTG in a similar manner to that described above to induce mutation, followed by culturing under the same conditions as described above by using a DM medium containing 8-hydroxyquinoline ($2\times10^{-4}$M) to obtain colonies, from which a mutant strain having an activity upon GSH-I and GSH-II and being released from the inhibition of GSH-I by glutathione, *E. coli* RC912 (FERM-BP No. 47), was obtained.

EXAMPLE 2

(1) Preparation of chromosome DNA which involves the genetic information of GSH-I (γ-glutamyl-L-cysteine synthetase)

A mutant strain of *Escherichia coli* designated *E. coli* RC912 (FERM-BP No. 47) induced from *E. coli* B 355 was cultured at 28° C. for 5 hours with shaking by using an L-medium [200 ml; having a composition of peptone (1%), yeast extract (0.5%), glucose (0.1%) and sodium chloride (0.5%); pH 7.2]. The resultant microbial cells were collected and washed with water. Then, the microbial cells were treated by the method of Saito and Miura [Biochim. Biophys. Acta, 72, 619–629 (1963)] using phenol to obtain chromosome DNA (900 μg).

(2) Preparation of vector DNA pBR 322 plasmid DNA which has genes responsible for the resistance to ampicillin and tetracycline was prepared in the following manner.

*Escherichia coli* B 355 (ATCC 23226), a host of pBR 322 plasmid was cultured at a pH of 7.2 and a temperature of 37° C. by using an L-medium as hereinbefore defined (1 l). At the later stage of the logarithmic growth phase ($OD_{660}$=about 0.3), chloramphenicol (150 μg/ml) was added to the medium and the culturing was further continued overnight. The microbial cells (3 g wet weight) were collected, washed with water, and then resuspended in 25 ml of 0.1M Tris-HCl (pH 8.0) containing 10 mM of EDTA. The lysis of the microbial cells was effected by treating with lysozyme (0.4 mg/ml) and sodium dodecylsulfate (1.4%) at 37° C. for one hour. The solution was centrifuged (35,000 r.p.m.; 2 hours) to obtain a supernatant which was treated with 2-butanol to concentrate the DNA. After this, DNA was treated with a ribonuclease (5 μg/ml) at 37° C. for 3 hours, followed by CsCl-Ethidium bromide (EtBr) ultracentrifugation (35,000 r.p.m.; 36 hours) to obtain pBR 322 plasmid DNA (450 μg).

(3) Insertion of chromosome DNA fragment into the vector

The chromosome DNA (1.5 μg) obtained by the step (1) was subjected to the reaction with a restriction enzyme Hin dIII (all of the restriction enzymes are products of Takara Shuzo Co.) (5 unit) at 37° C. for 1.5 hours and the vector DNA (1.0 μg) obtained by the step (2) was subjected to the reaction with a restriction enzyme Hin dIII (5 unit) at 37° C. for 6 hours to completely cut into pieces, respectively. Two reaction solutions were respectively heated at 65° C. for 10 minutes and were then mixed together. The combined solutions were treated with DNA ligase (2 unit, product of Takara Shuzo Co.) originating from $T_4$ phage at 10° C. for 16 hours to effect the insertion. After heating at 65° C. for 5 minutes, the reaction solution was added with ethanol ($\times$2 by volume), allowed to stand at $-20°$ C. for one hour and centrifuged (15,000 r.p.m.; 30 minutes) to collect the precipitates which were dissolved in a 5.0 mM tris-HCl buffered solution (pH 7.5; 0.15 ml) to obtain a DNA solution.

(4) Transformation by using plasmid carrying the genetic information of GSH-I

GSH-I deficient strain *E. coli* C 912 induced from *E. coli* B 355 (ATCC 23226) was cultured at 37° C. by using an L-medium as hereinbefore defined (50 ml). At the middle stage of the logarithmic growth phase ($OD_{660}$=about 0.30), the microbial cells were collected, washed twice with a tris-buffer solution (each 20 ml; 50 mM; pH 7.0) containing 50 mM of calcium chloride and was then suspended in a similar buffer solution (1.5 ml). To this suspension (0.2 ml) was added a DNA solution obtained by the step (3) (0.1 ml). The solution was kept at 0° C. for 20 minutes and immediately after this, a thermal puls (42° C.; 3 minutes) was exerted to the solution to make the introduction of the DNA into the cells. Then, the suspension was cultured with shaking at 37° C. for 120 minutes by using an L-medium as hereinbefore defined (pH 7.2; 3 ml). The microbial cells were collected, washed with water and spread on a DM agar medium [pH 7.0; composed of $KH_2PO_4$ (0.3%), $K_2HPO_4$ (0.7%), $MgSO_4.7H_2O$ (0.01%), $(NH_4)_2SO_4$ (0.1%), glucose (0.5%) and agar (1.5%) [20 ml/plate] containing tetramethylthiuramdisulfide (90 μg/ml) for culturing further at 28° C. for 24 hours. A transformed strain *E. coli* C 912p was obtained by determining the thus-obtained colonies with respect to their resistance to medicaments such as ampicillin, sensitivity to tetracycline and colour reaction using nitroprussideammonia. Finally, the amount of glutathione in the microbial cells and the activity of γ-glutamyl-L-cysteine synthetase (GSH-I) were determined for confirmation of the transformation.

(5) Self-cloning of plasmid carrying the genetic information of γ-glutamyl-L-cysteine synthetase The transformed strain C912p obtained by the step (4) was cultured by using an L-medium as hereinbefore defined [pH 7.2; 100 ml] at 37° C. ($OD_{660}$=about 0.3) and treated with chloramphenicol in a similar manner to that described in the above-mentioned step (2). After this, the microbial cells were collected, washed with 0.85% physiological solution of sodium chloride and treated by the method of Birnboim and Doly [Nucleic Acids Res., 7, 1513–1523 (1979)] to prepare a solution of pBR 322 plasmid (hereinafter referred to as pBR 322-gsh I) carrying the genetic information of γ-glutamyl-L-cysteine synthetase. The solution was subjected to DNA agarose electrophoresis (agarose 0.7%; 90 v; 5 hours) to cut up the band of pBR322-gsh I under irradiation of ultraviolet ray. The thus-obtained gel was put in a dialyzing tube and again subjected to the electrophoresis under the same conditions to extract DNA from the gel. The extracted solution (5 ml) was treated with 2-butanol to concentrate the DNA and remove the EtBr used for the electrophoresis. Then, to the solution was added ethanol (×2 by volume) to give precipitates of pBR322-gsh I (55 μg) which were dissolved in a tris-HCl buffer solution (5 mM; pH 7.5; 0.5 ml). *Escherichia coli* RC912 was treated in a similar manner to that described in the above-mentioned step (4) so as to enable the strain to incorporate the DNA and then the above-mentioned solution, pBR322-gsh I solution, was applied to incorporate pBR322-gsh I plasmid into the strain. Then, the strain was cultured at 37° C. for 16 hours by using a DM medium as hereinbefore defined (20 ml/plate; pH about 7.0) containing ampicillin (2.5 μg/ml) to form colonies, from which a transformed strain *E. coli* RC912p (FERM-BP No. 48) was obtained.

EXAMPLE 3

Strains shown in the following table were cultured, on each occasion, at 37° C. for 16 hours with shaking by using a medium (pH 7.0; 2 ml) having the composition of glucose (0.5%), $KH_2PO_4$ (0.3%), $K_2HPO_4$ (0.7%), $MgSO_4.7H_2O$ (0.01%) and $(NH_4)_2SO_4$ (0.1%). After completion of the culturing, the cultured broth was centrifuged (8,000 r.p.m./10 minutes) to collect the microbial cells which were washed with 0.85% physiological solution of sodium chloride, and glutathione was extracted from the microbial cells with water (1 ml) by heating to 100° C. The amount of glutathione in the extracted solution was measured to determine the glutathione accumulated (by μmole per one gram of the microbial cells). The results are shown in Table 1.

TABLE 1

| Strain | Accumulated glutathione (μmole/1 g of wet cells) |
|---|---|
| (Wild strain) *Escherichia coli* B 355 | 1.8 |
| (Revertant) *E. coli* RC912 (FERM-BP 47) | 2.8 |
| (Strain of the present invention) *E. coli* RC912p (FERM-BP 48) | 7.9 |

EXAMPLE 4

Strains shown in the following Table 2 were respectively cultured in a similar manner to that described in Example 3. After completion of the culturing, on each occasion, the microbial cells were collected by centrifugation (8,000 r.p.m./10 min.) of the cultured broth and were then subjected to ultrasonic treatment (90 KHz/5 min.) to prepare a cell-free extract. This cell-free extracted solution (0.05 ml) was added to a 50 mM tris buffer solution (9.95 ml; pH 7.5) containing L-glutamic acid (25 mM), L-cysteine (25 mM), glycine (50 mM), magnesium chloride (10 mM), acetylphosphate (10 mM) and ATP (5 mM) to effect the enzymatic reaction at 37° C. for one hour. After completion of the reaction, the amount of glutathione formed in the reaction solution was measured to determine the accumulated amount of glutathione per one mg of protein. The results are shown in the following table.

TABLE 2

| Strain | Accumulated amount of glutathione (μmole/1 mg of protein) |
|---|---|
| (Wild strain) *Escherichia coli* B 355 | 0.11 |
| (Revertant) *E. coli* RC912 (FERM-BP 47) | 0.54 |
| (Strain of the present invention) *E. coli* RC912p (FERM-BP 48) | 1.96 |

We claim:

1. A mutant strain *Escherichia coli* RC 912p (FERM-BP 48) which produces γ-glutamyl-L-cysteine synthetase which is not inhibited by glutathione and glutathione synthetase, and is thereby capable of producing glutathione.

2. A process for the preparation of glutathione which comprises culturing mutant strain *Escherichia coli* RC 912p (FERM-BP48) in a medium to accumulate glutathione in the cultured broth, and recovering the resultant glutathione therefrom.

3. The process of claim 2 wherein culturing is effected at a pH of 6 to 9 and a temperature of 25° to 37° C. under aerobic conditions.

4. The process of claim 2 wherein glutathione accumulated in the microbial cells is extracted with hot water.

5. A process for the preparation of glutathione which comprises culturing a mutant strain *Escherichia coli* RC 912p (FERM-BP48) in a medium to accumulate γ-glutamyl-L-cysteine synthetase and glutathione synthetase in a cultured broth, contacting the resultant enzymes with a substrate solution containing L-glutamic acid, L-cysteine and glycine to effect an enzymatic reaction to form glutathione, and recovering the resultant glutathione from the reaction solution.

6. The process of claim 5 wherein the concentrations of reactions in the substrate solution are as follows:
L-glutamic acid 5 to 50 mM
L-cysteine 5 to 50 mM
glycine 50 to 10 mM.

7. The process fo claim 5 wherein the reaction is effected at a pH of 6 to 9 and a temperature of 20° to 50° C.

8. The process of claim 5 wherein the reaction is carried out in the presence of an adenosine-5'-triphosphate (ATP) regeneration system.

* * * * *